United States Patent [19]

Carter et al.

[11] Patent Number: 5,628,890
[45] Date of Patent: May 13, 1997

[54] ELECTROCHEMICAL SENSOR

[75] Inventors: Nigel F. Carter, Oxon; Geoffrey R. Chambers, Northwood Middlesex; Graham J. Hughes, Oxford; Steven Scott, Oxon; Gurdial S. Sanghera, Oxford; Jared L. Watkin, Oxon, all of England

[73] Assignee: MediSense, Inc., Waltham, Mass.

[21] Appl. No.: 534,876

[22] Filed: Sep. 27, 1995

[51] Int. Cl.⁶ .................................................. G01N 27/26
[52] U.S. Cl. .................. 204/403; 204/415; 204/418; 435/4; 435/817; 435/287.1; 435/287.9
[58] Field of Search ......................... 204/403, 415, 204/418; 435/288, 291, 817, 4

[56] References Cited

U.S. PATENT DOCUMENTS

| | | | |
|---|---|---|---|
| 4,053,381 | 10/1977 | Hamblen et al. | 204/195 M |
| 4,137,495 | 1/1979 | Brown | 324/30 B |
| 4,413,407 | 11/1983 | Columbus | 29/825 |
| 4,549,952 | 10/1985 | Columbus | 204/416 |
| 4,591,550 | 5/1986 | Hafeman et al. | 435/4 |
| 4,897,173 | 1/1990 | Nankai et al. | 204/403 |
| 4,935,119 | 6/1990 | Yamada et al. | 204/425 |
| 4,966,671 | 10/1990 | Nylander et al. | 204/153.14 |
| 5,021,140 | 6/1991 | Sato | 204/416 |
| 5,064,618 | 11/1991 | Baker et al. | 422/82.01 |
| 5,120,420 | 6/1992 | Nankai et al. | 204/403 |
| 5,141,868 | 8/1992 | Shanks et al. | 435/288 |
| 5,192,415 | 3/1993 | Yoshioka et al. | 204/403 |
| 5,234,813 | 8/1993 | McGeehan et al. | 435/7.9 |
| 5,264,103 | 11/1993 | Yoshioka et al. | 204/403 |

(List continued on next page.)

FOREIGN PATENT DOCUMENTS

| | | |
|---|---|---|
| 0021798A2 | 1/1981 | European Pat. Off. . |
| 0078636B1 | 5/1983 | European Pat. Off. . |
| 0122420B1 | 10/1984 | European Pat. Off. . |
| 0121385A1 | 10/1984 | European Pat. Off. . |
| 0127958A2 | 12/1984 | European Pat. Off. . |
| 0136362A1 | 4/1985 | European Pat. Off. . |
| 0170375B1 | 2/1986 | European Pat. Off. . |
| 0186286A1 | 7/1986 | European Pat. Off. . |
| 0226470A2 | 6/1987 | European Pat. Off. . |
| 0230645A2 | 8/1987 | European Pat. Off. . |
| 0230472A1 | 8/1987 | European Pat. Off. . |
| 0255291A1 | 2/1988 | European Pat. Off. . |
| 0267724A1 | 5/1988 | European Pat. Off. . |
| 0274215A1 | 7/1988 | European Pat. Off. . |
| 0291194B1 | 11/1988 | European Pat. Off. . |
| 0351891B1 | 1/1990 | European Pat. Off. . |
| 0470649A2 | 2/1992 | European Pat. Off. . |
| 2127142 | 12/1971 | Germany . |
| 1318815 | 5/1971 | United Kingdom . |
| WO92/17778 | 10/1992 | WIPO . |

OTHER PUBLICATIONS

Polymeric Materials Science and Engineering American Chem. Society, 61:683–689, 1989, Miami Beach, Florida no month available.

*Primary Examiner*—Bruce F. Bell
*Attorney, Agent, or Firm*—Fish & Richardson P.C.

[57] ABSTRACT

An electrode strip for use in an electrochemical sensor for measuring a compound in a sample is provided, including an electrode support, a reference or counter electrode disposed on the support, a working electrode spaced from the reference or counter electrode on the support, a covering layer defining an enclosed space over the reference and working electrodes and having an aperture for receiving a sample into the enclosed space, and a plurality of mesh layers interposed in the enclosed space between the covering layer and the support, the covering layer having a sample application aperture spaced from said electrodes and said reference electrode spaced from said working electrode at a position remote from and on the opposite side of said working electrode from said aperture. The working electrode includes an enzyme capable of catalyzing a reaction involving a substrate for the enzyme or a substrate catalytically reactive with an enzyme and a mediator capable of transferring electrons transferred between the enzyme-catalyzed reaction and the working electrode to create a current representative of the activity of the enzyme and representative of the compound.

21 Claims, 4 Drawing Sheets

U.S. PATENT DOCUMENTS

| | | | |
|---|---|---|---|
| 5,266,179 | 11/1993 | Nankai et al. | 204/401 |
| 5,332,479 | 7/1994 | Uenoyama et al. | 204/403 |
| 5,354,447 | 10/1994 | Uenoyama et al. | 204/403 |
| 5,382,346 | 1/1995 | Uenoyama et al. | 204/403 |
| 5,395,504 | 3/1995 | Saurer et al. | 204/403 |
| 5,407,554 | 4/1995 | Saurer | 204/403 |
| 5,496,453 | 3/1996 | Uenoyama et al. | 204/403 |

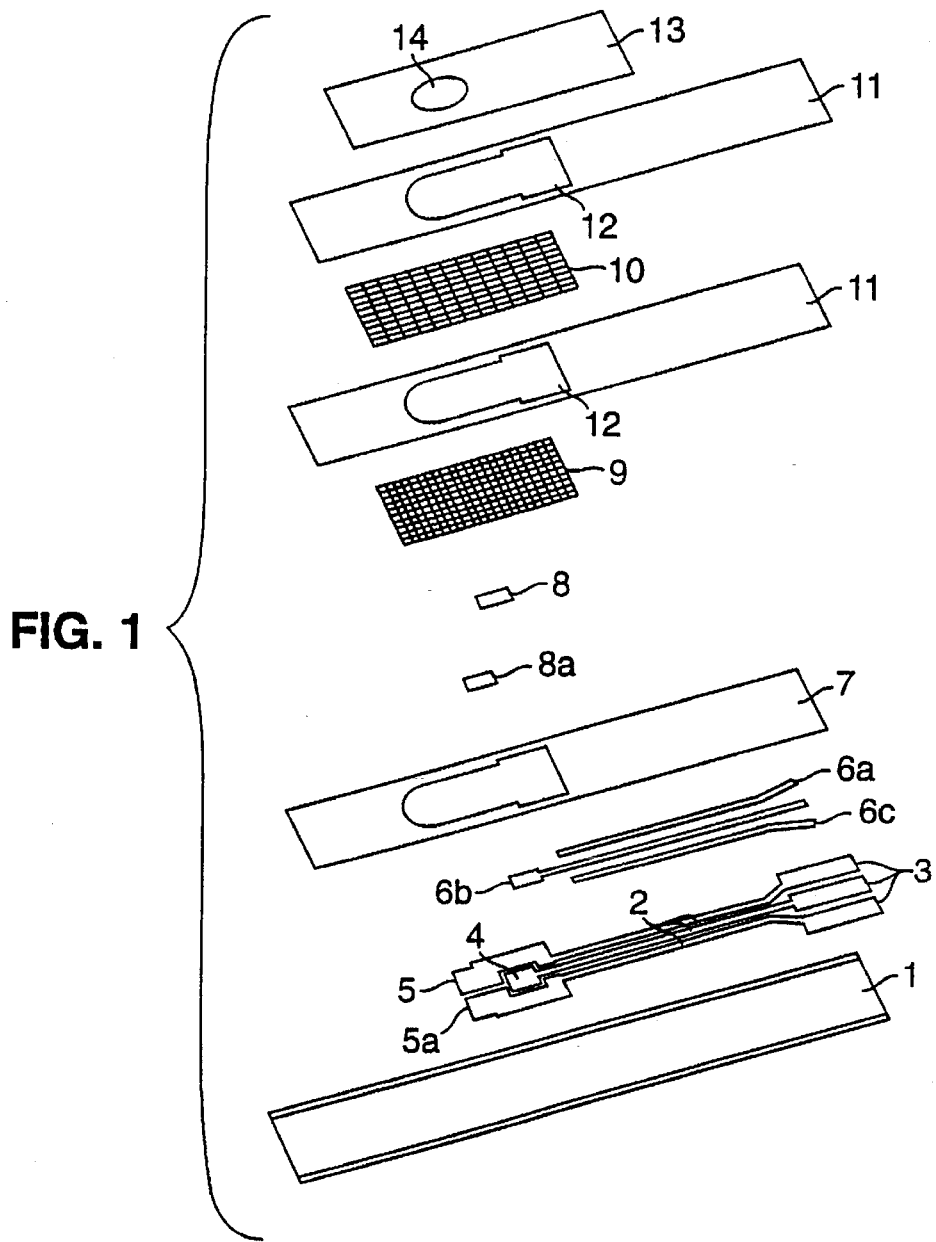
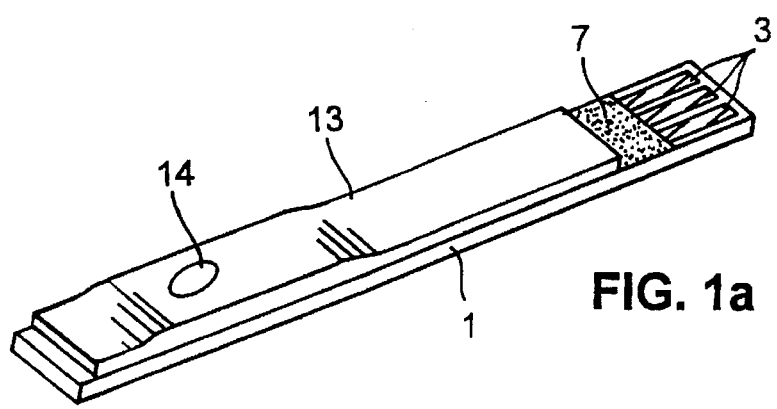

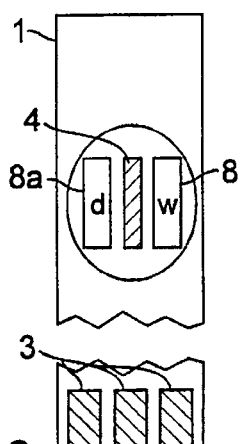
FIG. 2
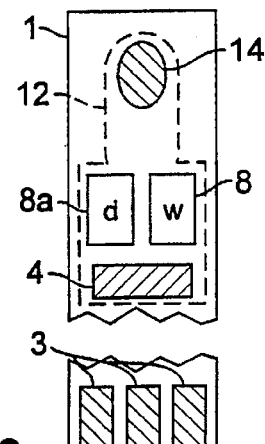
FIG. 2a
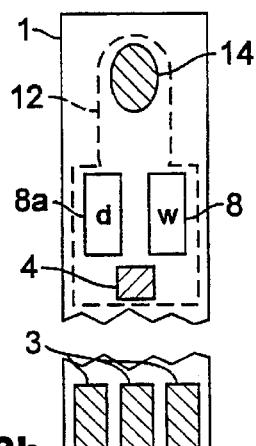
FIG. 2b
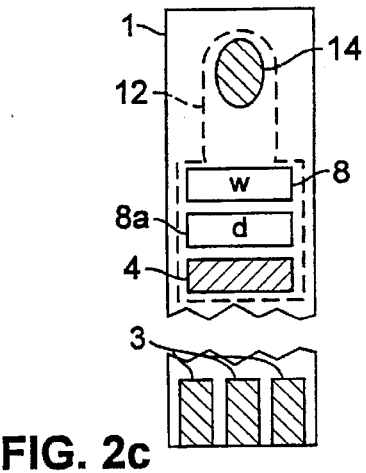
FIG. 2c
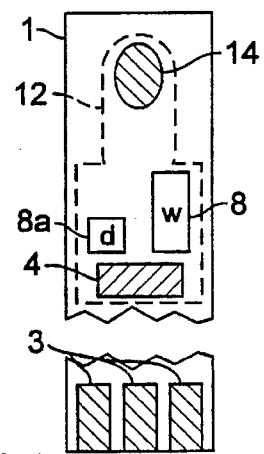
FIG. 2d
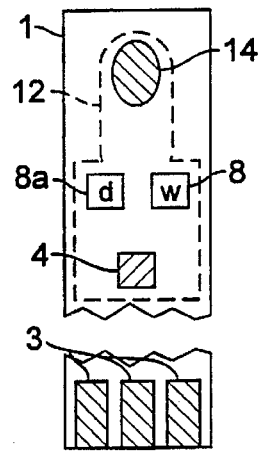
FIG. 2e
 SAMPLE APPLICATION POINT    WORKING ELECTRODE
 REFERENCE ELECTRODE    DUMMY ELECTRODE

ELECTROCHEMICAL SENSOR

BACKGROUND OF THE INVENTION

This invention relates to sensors for performing electrochemical assays for the accurate determination of one or more enzymes or their substrates in complex liquid mixtures. The invention is of particular utility for biomedical applications in whole blood.

The measurement of dissolved analytes in whole blood is subject to interference by red cells (hematocrit) due to the volume exclusion of the non-liquid fraction of the cells. In addition, where a rate reaction based upon the turnover of the analytes by a specific enzyme is utilized to measure analyte concentration, measurement is subject to the restriction of the diffusional pathways for the analyte and enzyme by the red cell fraction. This interference tends to cause an artificially high response rate for low hematocrit levels, and, conversely, an artificially low response rate for high hematocrit levels.

A common method for overcoming this interference is to filter out or otherwise separate off the red cells and measure the concentration of the analyte in plasma, or to pretreat the whole blood sample to reduce or eliminate the red cell volume (e.g. by lysis of the cells). However, the incorporation of a sample pre-treatment step or the requirement to separate off the red cell fraction in a whole blood sample does not give rise to measurement devices which are simple and convenient to use outside of the analytical laboratory.

Another problem encountered with some electrode strips used with electrochemical sensors is that application of an insufficient amount of sample to the electrodes tends to produce an artificially low response due to the failure to completely cover the working electrode with sample. Moreover, even if a sufficient amount of sample is initially applied to the strip, if the strip is not held in a horizontal position the sample can flow off of the strip, and/or the electrode area may not be wetted by the sample due to the surface tension of the sample.

U.S. patent applications Ser. Nos. 08/281,131 and 08/281,237 and European Patents Nos. 127,958 and 351,891 describe the construction of sensors comprising a conductive electrode coated with a mixture, or layers, of a catalytically active enzyme and a mediator compound. When such a coated electrode is contacted with a liquid sample containing a species for which the enzyme exerts a catalytic effect, the mediator compound transfers electrons from the reaction and the resulting current can be used to give a readout signal relating to the concentration of the said substrate. Alternatively, a substrate can be used in the mixture instead of an enzyme when it is desired to measure an enzyme which exerts a catalytic effect on the substrate.

Such sensors are used in the chemical industry, e.g., to analyze complex mixtures, for example in the food industry and in biochemical engineering, and are also valuable in biological investigation in human or animal medicine. The sensors may be used as invasive probes, i.e., one that can be inserted into the body and make contact with a body fluid such as whole blood or subcutaneous fluid. Alternatively the electrode system may be used as part of an external test upon a withdrawn sample (e.g., blood withdrawn by a syringe) or upon an expressed sample (e.g., blood obtained using a needle pricking device).

SUMMARY OF THE INVENTION

In one aspect, the invention features an electrode strip for use in an electrochemical sensor for measuring a compound in a sample, the electrode including an electrode support, a reference or counter electrode disposed on the support, a working electrode spaced from the reference or counter electrode on the support, a covering layer defining an enclosed space over the reference and working electrodes and having an aperture for receiving a sample into the enclosed space, and a plurality of mesh layers interposed in the enclosed space between the covering layer and the electrodes. The working electrode includes either an enzyme capable of catalyzing a reaction involving a substrate for the enzyme or a substrate catalytically reactive with an enzyme and a mediator capable of transferring electrons transferred between the enzyme-catalyzed reaction and the working electrode to create a current representative of the activity of the enzyme or substrate and representative of the compound.

In another aspect, the invention features an electrode strip for use in an electrochemical sensor for measuring a compound in a sample, including an elongated electrode support defining a sample transfer path for directional flow of the sample from an application point along the support, a working electrode in the sample transfer path, and a reference or counter electrode downstream of any portion of the working electrode in the sample transfer path.

Preferably, the mesh layers have different mesh sizes. More preferably, the mesh layers comprise a first layer adjacent the electrodes and a second mesh layer interposed between the first layer and the covering layer, the second layer having a coarser mesh size than the first layer. Preferred mesh layers are formed of woven material and are surfactant coated, with the first layer containing a higher loading of surfactant than the second layer. Preferred strips further include an area of solid hydrophobic insulating material disposed around the periphery of the electrodes. The mesh layers preferably define a path for directional flow of sample from the aperture through the enclosed space towards the working and reference electrodes, and control sample thickness above the working and reference electrodes.

In preferred embodiments, the electrochemical sensor reduces the effect of hematocrit, on response rate. This results from the downstream spacing of the reference electrode relative to the working electrode in combination with the thin layer of the sample solution created by the mesh layers. Thus, the accuracy of the response indicated by the sensor is improved. This feature is useful not only when whole blood is the sample to be analyzed, but also with other complex solutions which contain large molecules that can interfere with diffusion.

The sensors of the invention also tend to reduce or prevent inaccurate results due to inadequate sample volumes by providing a mechanism which prevents any response from being detected if sample volume is too low to provide an accurate reading. Because the reference electrode is downstream from the working electrode, a circuit is not established until the working electrode has been completely covered by sample and sample has reached the reference electrode, and thus no response will be detected if the sample size is inadequate to cover the working electrode. This feature is enhanced by the provision, in preferred embodiments, of mesh layers which move the sample towards the working electrode and reference electrode in a uniform manner, ensuring that no sample will reach the reference electrode until the working electrode is completely covered.

Additionally, the enclosed nature of the preferred sensors, the mesh layers, and the hydrophobic areas of the outer surface of the sensor combine to reduce the sensitivity of the sensor strip to the angle at which it is held and the resistance of the sample to wetting of the electrode area.

Other features and advantages of the invention will be apparent from the description of the preferred embodiment thereof, and from the claims.

BRIEF DESCRIPTION OF THE DRAWING

FIG. 1 is an exploded view of an electrode strip according to one embodiment of the invention FIG. 1a is a perspective view of the assembled strip of FIG. 1.

FIG. 2 is a plan view of a control electrode strip in accordance with prior art. FIGS. 2a–2e are plan views of a number of preferred embodiments for the arrangement of the working, dummy and reference electrodes in relation to a sample application point.

FIG. 5a shows the results given by a preferred embodiment of the invention; FIG. 5b shows the results for a control strip.

DESCRIPTION OF THE PREFERRED EMBODIMENTS

Figure 3:
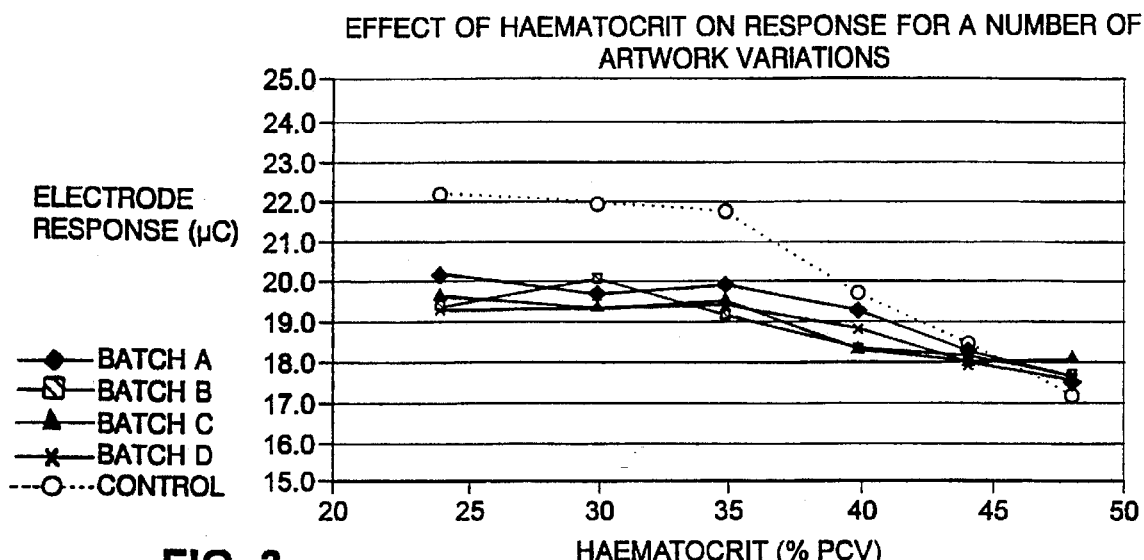
FIG. 3 is a graph showing the effect of the whole blood hematocrit at a given glucose level on the electrode response given by both a control strip and a number of strips according to different embodiments of the invention.

A preferred electrode sensor strip is shown in FIGS. 1–1a. The electrode support 1, typically an elongated strip of plastic material, e.g., PVC, polycarbonate or polyester, supports two or more printed tracks of electrically conducting carbon ink 2. These printed tracks define the positions 4 of the reference or counter electrode, 5 and 5a of the working and dummy electrodes, and of the electrical contacts 3 that are inserted into an appropriate measurement device (not shown).

The elongated portions of the conductive tracks are each overlaid with a silver/silver chloride track 6a, 6b (forming the reference electrode), and 6c, and further overlaid with a layer of hydrophobic electrically insulating material 7 that leaves exposed only the positions of the reference/counter electrode, the working and the dummy electrodes, and the contact areas. This hydrophobic insulating material serves to prevent short circuits and to physically define the working/reference electrode area. Because this insulating material is hydrophobic, it also serves to confine the sample to the exposed electrodes. A preferred insulating material is available under the tradename POLYPLAST from Sericol Ltd., Broadstairs, Kent, UK.

The electrodes 8, 8a, formed of a mixture of an enzyme, a mediator and a conductive material (the working electrode 8) and a mixture of a mediator and a conductive material without enzyme (the dummy electrode 8a), are applied to the positions 5, 5a of carbon tracks 2, usually by printing, as discrete areas of fixed length. Alternatively, electrode 8, instead of an enzyme, can contain a substrate catalytically reactive with an enzyme to be detected. The conductive material in a preferred embodiment comprises particulate carbon having adsorbed thereon the mediator. For printing, a printing ink is formed as an aqueous solution of the conductor and adsorbed mediator, which, for the working electrode, also includes the enzyme. When the analyte to be tested is glucose in blood, preferably the enzyme is glucose oxidase and the mediator is a ferrocene derivative.

The reference electrode 6b is situated relative to the working and dummy electrodes 8, 8a such that it is in a non-ideal position for efficient electrochemical function, i.e., the electrodes are arranged not to minimize the effect of the resistance of the solution on the overall resistance of the circuit, as is conventional, but so that solution resistance is maximized to the extent possible while still being able to generate a current response with the measurement device used. To increase solution resistance, the reference electrode is spaced as far as possible from the working electrode within the constraints of the maximum solution resistance which will still allow a current response to be generated while minimizing the sample volume that must be used (the electrodes cannot be spaced so far apart that they cannot both be covered by the sample). Conversely, ideally the sample path length will be kept as short as possible, so that the sample volume required is minimized, but its maximum length can be as great as the length of the strip that can accommodate it, limited, however, by the resulting increase in solution resistance, to a distance which allows the current response to be generated. The solution resistance is also influenced by the length of the edge to edge cross-sectional area between the reference electrode and the working and dummy electrodes. Minimizing this length, by positioning the reference electrode downstream of the working electrode rather than positioning the electrodes contiguously, as is conventional, increases the solution resistance. Positioning the electrodes in this manner has the further benefit of preventing completion of a circuit (and thus detection of a response) before the working electrode has been completely covered by sample, as explained hereinabove.

There are many electrode configurations which can be used, a number of which are shown in FIGS. 2a–2e. The preferred embodiments are those where the reference electrode 6b lies downstream (in the direction of sample flow) of the working electrode 8 and a remote application point at an aperture 14 for the sample is provided upstream of the reference electrode, especially as shown in FIG. 2b. In a particular embodiment similar to that illustrated in FIG. 2b, the working and dummy electrodes are spaced from the reference electrode about 0.35 mm. apart in the direction of sample flow. The working and dummy electrodes have a width of about 1 mm, and a length of about 2 mm. The reference electrode has dimensions of about 1.5 mm×1.5 mm.

The electrode area is then overlaid by a fine grade surfactant coated mesh 9 which serves to protect the printed components from physical damage and help the sample to wet the reference and working electrodes by reducing the surface tension of the sample and therefore allowing it to spread evenly over the electrodes. In a preferred embodiment this mesh layer extends over the whole length of the sample path, between and including the application point and the electrode area. Preferably this mesh will be constructed of finely woven nylon strands, but any woven or non woven material may be used provided it does not occlude the surface of the electrode such that the normal diffusional processes are obstructed. The thickness of the mesh is selected so that the maximum sample depth provided by this mesh and the second layer overlying it, discussed below, is sufficiently small to produce a high solution resistance. Generally it is preferred that the fabric be not more than 70 μm in thickness. Preferably the mesh has a percent open area of from about 40 to 45%, a mesh count of about 95 to 115 per cm, a fiber diameter of from about 20 to 40 μm, and a thickness of from about 40 to 60 μm. A particularly preferred mesh is NY64 HC mesh, available from Sefar (formerly ZBF), CH-8803, Ruschlikon, Switzerland.

It is only necessary that the mesh be surfactant coated if the mesh material itself is hydrophobic in nature (for example nylon or polyester); if a hydrophilic mesh were used the surfactant coating could be omitted. Any suitable surfactant may be used to coat the mesh so long as it allows adequate even spreading of the sample. A preferred surfactant is FC 170C FLUORAD fluorochemical surfactant, available from 3M, St. Paul, Minn., which is a solution of a fluoroaliphatic oxyethylene adduct, lower polyethylene glycols, 1,4-dioxane and water. A preferred surfactant loading for most applications is from about 15–20 μg/mg of mesh. The preferred surfactant loading may vary depending on the type of mesh and surfactant used and the sample to be analyzed, but can be determined empirically by observing flow of the sample through the mesh with different levels of surfactant.

The mesh layer 9 is held down and fixed in place by a layer of hydrophobic electrically insulating ink 11. This layer is preferably applied by screen printing the ink over a portion of the periphery of the mesh which surrounds and defines a suitable sample transfer path 12 for the sample to travel from the application point at the furthest end of the strip towards the working and reference electrodes, the ink impregnating the mesh outside of path 12.

A second layer of coarser surfactant coated mesh 10 is applied over the first mesh. This second mesh layer controls the influx of the sample as it travels from the application point towards the reference and working electrode areas by providing a space into which the displaced air within the sample transfer path can move as the sample moves preferentially along the lower fine grade mesh layer 9 and partially in mesh layer 10. The spacing of the larger fibers of the secondary mesh layer, perpendicular to the direction of flow of the sample, further helps to control the flow of the sample by presenting repeated physical barriers to the movement of the sample as it travels through the transfer path. The regular pattern of the mesh fibers ensures that the sample progresses in stages and that only samples with sufficient volume to generate an accurate response are able to pass all the way along the pathway and reach the reference electrode.

It is preferred that mesh 10 be of a woven construction, so that it presents a regular repeating pattern of mesh fibers both perpendicular to and parallel to the longest aspect of the strip. Generally the second mesh layer should be substantially thicker than the first mesh, with larger diameter mesh fibers and larger apertures between them. The larger mesh preferably has a thickness of from 100 to 1000 μm, with a thickness of from 100 to 150 μm being most preferred. A preferred mesh has a percent open area of about 50 to 55%, a mesh count of from about 45 to 55 per cm, and a fiber diameter of from about 55 to 65 μm. A preferred mesh is NY151 HC mesh, also available from Sefar, CH-8803, Ruschlikon, Switzerland.

Mesh 10 is also provided with a coating of a suitable surfactant (unless the mesh itself is hydrophilic), preferably the same surfactant as that on the first mesh layer. The loading of surfactant is lower on mesh 10 than on mesh 9, providing a further barrier to movement of sample past the transverse fibers of mesh 10. In general, a loading of 1–10 μg/mg of mesh is preferred.

The second mesh layer 10 is held in place by a second layer of the hydrophobic electrically insulating ink 11, applied to the same portion of the mesh as to which it is applied to mesh layer 9, i.e., surrounding the sample transfer path. The insulating material thus defines sample is transfer path 12 by not allowing sample to infiltrate the area of mesh covered by the layers of insulating material, the insulating material impregnating the mesh outside of path 12. A preferred insulating ink for impregnating both the first and second mesh layers is available from Sericol, Ltd., Broadstairs, Kent, UK, under the tradename SERICARD.

Finally, the upper part of the electrode is enclosed by a liquid/vapor impermeable membrane 13 (typically a flexible tape made of polyester or similar material) which includes a small aperture 14 to allow access of the applied sample to the underlying surfactant coated mesh layers. This impermeable membrane serves to enclose the exposed working and reference electrodes and thus maintain the available sample space over the electrodes at a fixed maximum height equivalent to the thickness of both mesh layers, ensuring that the solution resistance is kept at a high level. Any sample thickness up to the maximum depth of the two mesh layers has been found to be adequate in this respect. Aperture 14 is positioned overlying the furthest end of the open mesh area, remote from the reference electrode 6b, such that the exposed area of mesh beneath the aperture can be used as a point of access or application for the liquid sample to be measured. This aperture can be of any suitable size large enough to allow sufficient volume of sample to pass through to the mesh layers, but should not be so large as to expose any of the working/reference electrode area. The aperture is formed in the tape layer by any suitable method, e.g., die punching. The tape layer is affixed to the strip along specific areas, not including the working/reference electrodes, the sample transfer path or application area, using a suitable method of adhesion. Preferably this is achieved by coating the underside of a polyester tape with a layer of hot melt glue which is then heat welded to the electrode surface. The hot melt glue layer is typically of a coating weight between 10–50 g/m$^2$, preferably from 20 to 30 g/m$^2$. Pressure sensitive glues or other equivalent methods of adhesion may also be used.

The upper surface of the tape layer can also be usefully provided with a layer of silicone or other hydrophobic coating which helps to drive the applied sample onto the portion of exposed surfactant coated mesh at the application point and thus make the application of small volumes of sample much simpler.

Accordingly, in use, a sensor strip of the invention is connected, via electrode contacts 3, to a measuring device (not shown). Then a sample is applied to aperture 14, and moves along the sample transfer path 12 in mesh layer 9 and partially in mesh layer 10, its progress being sufficiently impeded by mesh layer 10 to allow the sample to form a uniform front rather than flowing non-uniformly. Air is displaced through the upper portion of mesh layer 10 to and through aperture 14. The sample first covers working electrode 5 in its entirety, and only then approaches and covers reference electrode 4, completing the circuit and causing a response to be detected by the measuring device.

The following examples are intended to be illustrative and not limiting in effect.

EXAMPLE 1

Demonstration of Hematocrit Compensation in a Single Whole Blood Sample

Sample strips were constructed with a number of different geometric configurations (FIGS. 2a–2e) such that the reference electrode was positioned at a sufficient distance away from the working electrode to produce a high level of uncompensated solution resistance. These were then overlaid with mesh and tape layers to produce a thin layer cell as described previously. Control strips (FIG. 2) which had an open aspect and closely adjacent working and reference electrodes were tested alongside the sample electrodes.

A sample of venous blood was collected to separate the plasma and red cell phases. These were then recombined with different proportions of red cells added back to the plasma to produce a range of smaller aliquots of blood of various hematocrit levels (as defined by the relative proportion of red cells—% PCV). All the aliquots showed the same glucose level when measured by a YSI (Yellow Springs Instruments, Inc.) blood glucose analyzer.

Figure 4:
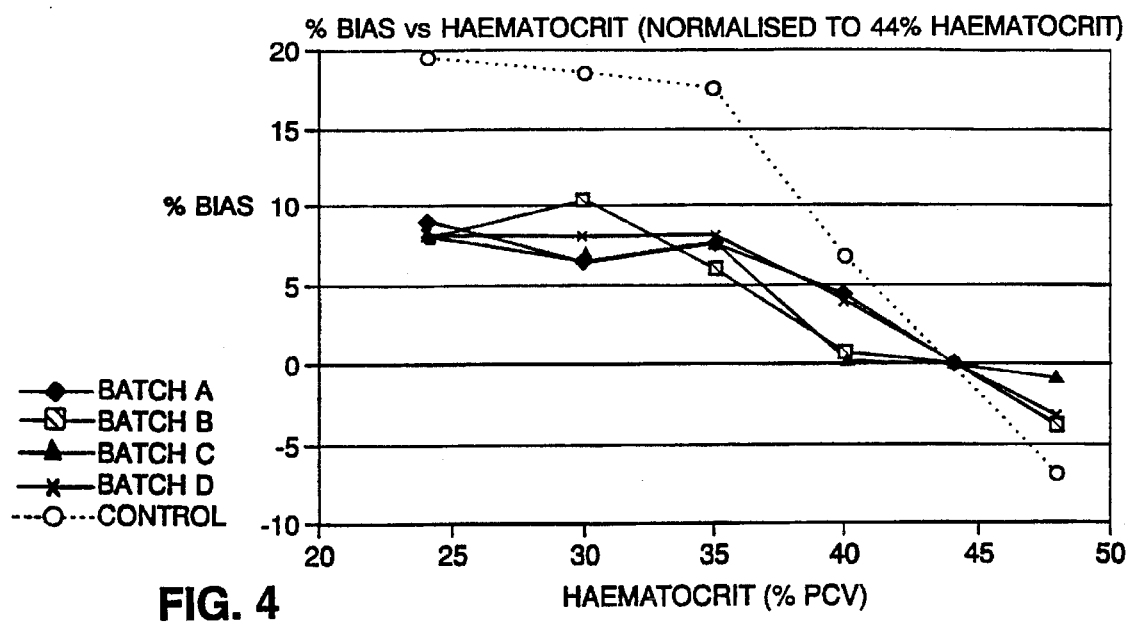
FIG. 4 is a graph showing the percentage bias of the measured glucose result from the actual glucose level in the sample given by both a control strip and a number of strips according to various embodiments of the invention. The results were normalized to the 44% hematocrit level.

Small volumes of each of the aliquots of adjusted hematocrit blood were applied to the target area of the sample and control strips and allowed to cover the working and reference electrodes. The responses of the strips to the glucose concentration in the blood were measured after a steady state response was achieved, using the appropriate meter for which the electrodes were compatible. The measured steady state responses were compared for each of the different hematocrit blood samples such that the relationship between the hematocrit level of the blood and the electrode response could be plotted graphically. The results are shown in FIG. 3. The responses were also converted to a percentage ratio (bias) of the response at the original hematocrit of the blood sample (44%) to better directly compare the difference between the control and the sample strips. These results are shown in FIG. 4. Both figures show a much reduced range (approximately 504) of response/bias for the sample strips over the control strips, demonstrating reduction in hematocrit sensitivity caused by the uncompensated solution resistance.

EXAMPLE 2

Demonstration of Hematocrit Compensation in a Series of Whole Blood Samples

Figure 5A:
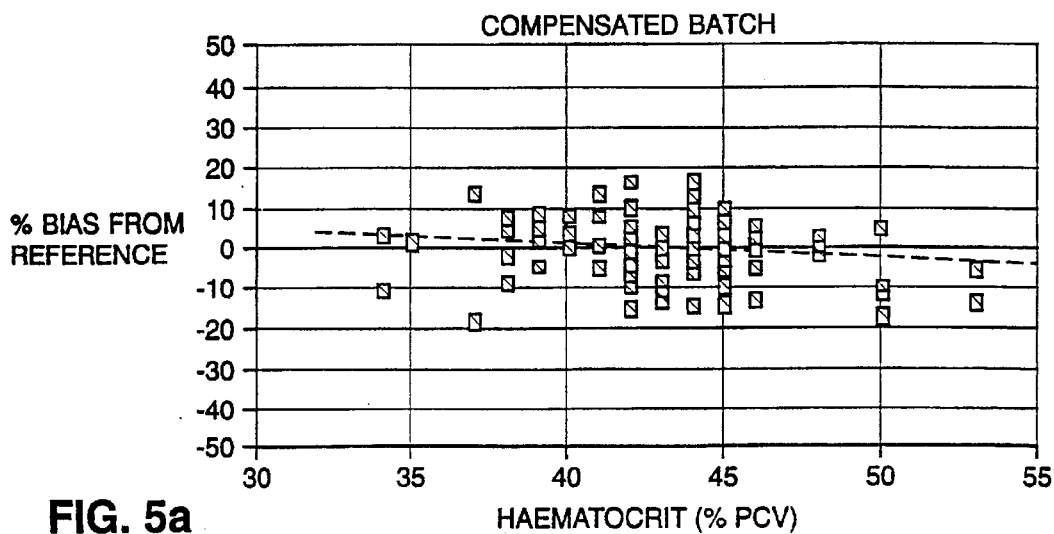
FIGS. 5a and 5b are graphs showing the effect of hematocrit on the percentage bias of the calibrated whole blood glucose result from the actual glucose level in a range of patient samples of different blood glucose and hematocrit levels.
Figure 5B:
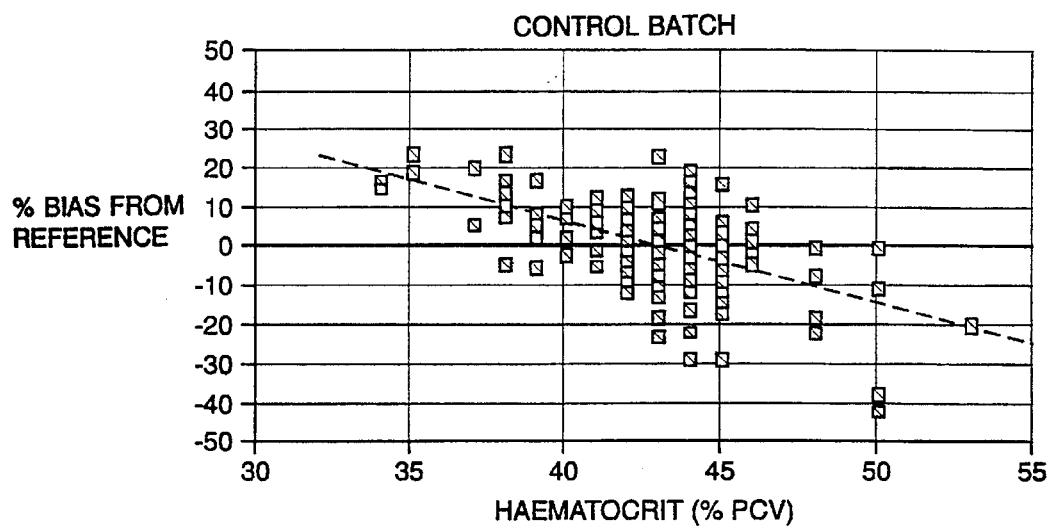

Strips with the geometric configuration shown in FIG. 2b were overlaid with mesh and tape layers to produce a thin layer cell as described previously. These were tested using capillary blood taken from the fingers of 40 diabetic patients presenting a wide range of blood glucose and hematocrit values. The responses were compared against those of a YSI blood glucose analyzer and the percentage bias of the individual results calculated and plotted against its measured hematocrit. FIGS. 5a and 5b show how the spread of percentage bias values over the hematocrit range is much reduced where the uncompensated solution resistance has compensated for the hematocrit induced bias of each blood sample.

Thus, the hematocrit compensation does not rely upon an algorithm or the measurement of the hematocrit of the individual sample in order to work, but is a natural compensating mechanism that uses the inherent solution resistance of the sample which is in turn dependent primarily upon the concentration of red blood cells in the sample. Accordingly, different samples are in effect self compensating.

EXAMPLE 3

Demonstration of the Minimum Sample Volume Control Feature

Figure 6:
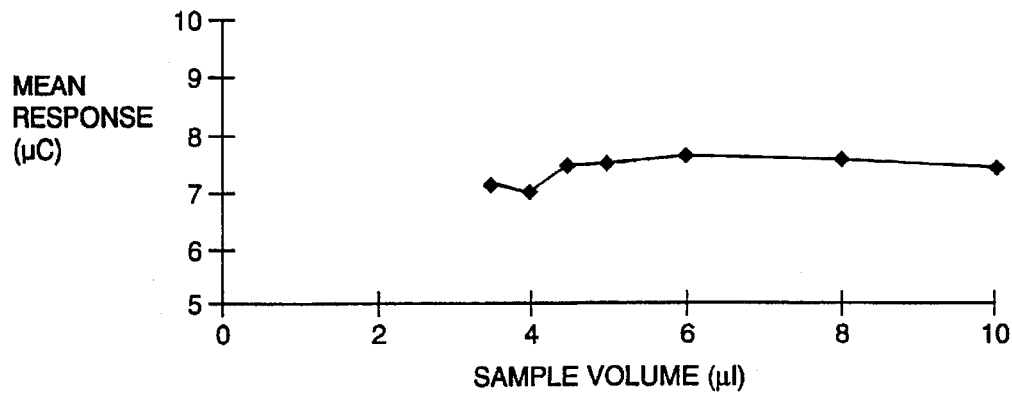
FIG. 6 is a graph showing the average response given by a strip according to one embodiment of the invention to samples of progressively smaller volumes.

Strips with the geometric configuration shown in FIG. 2b were overlaid with mesh and tape layers to produce a thin layer cell as described previously. Blood samples of progressively smaller volumes were applied to the strips and the responses measured. The results were as shown in FIG. 6. There was no dependence of the response on the sample volume and below 3 µl volume there was no response from the strips. Because the passage of the sample along the sample path through the fine grade mesh is controlled by the thicker fibers of the second mesh perpendicular to the flow direction, the penetration of the sample along the sample pathway must be driven by the amount of sample applied. Very low sample volumes will mean that the sample will only travel a partial distance, but the fibers of the second mesh will ensure that the leading edge will be maintained as a uniform front. Because the assay will only start when there is a current detected between the working electrode and the reference electrode through the conductivity of the sample, with the reference electrode situated behind the working electrode the assay will only start after the working electrode has been completely covered by the sample. Sample volumes that are too small to completely cover the working electrode area therefore do not start the assay.

Other embodiments are within the claims. For example, the enzyme/mediator combination utilized in the embodiments described above is glucose oxidase mediated by a ferrocene derivative. This combination is particularly suitable for the measurement of glucose in a blood sample. Many other combinations of enzymes/mediators or substrates/mediators capable of generating a faradaic current could be selected, however, to measure other analytes, as would be understood by one skilled in the art.

What is claimed is:

1. An electrode strip for use in an electrochemical sensor for measuring a compound in a sample, comprising:

an electrode support;

a reference or counter electrode disposed on the electrode support;

a working electrode spaced from the reference or counter electrode on the electrode support and comprising an enzyme which catalyzes a reaction involving a substrate for said enzyme or a substrate catalytically reactive with an enzyme and a mediator which transfers electrons between said enzyme-catalyzed reaction and said working electrode to create a current representative of the activity of said enzyme and representative of the compound;

a covering layer defining an enclosed space over the reference and working electrodes, said covering layer having an aperture for receiving a sample into said enclosed space; and a plurality of mesh layers interposed in said enclosed space between said covering layer and said electrodes.

2. The strip of claim 1 wherein said mesh layers are surfactant coated.

3. The strip of claim 1 wherein said mesh layers define a path for directional flow of sample from said aperture through said enclosed space towards said working and reference electrodes, and said reference electrode is downstream from said working electrode in the direction of said flow.

4. The strip of claim 1 wherein said mesh layers have different mesh sizes.

5. The strip of claim 4 wherein said mesh layers comprise a first layer adjacent said electrodes and a second mesh layer interposed between said first layer and said covering layer, said second layer having a coarser mesh size than said first layer.

6. The strip of claim 5 wherein at least said second layer is formed of woven material.

7. The strip of claim 5 wherein said mesh layers are surfactant coated, and said first layer contains a higher loading of surfactant than said second layer.

8. The strip of claim 7 wherein said mesh layers are of hydrophobic material and said surfactant coatings on said layers render them hydrophilic.

9. The strip of claim 7 wherein at least said second layer is formed of woven material.

10. The strip of claim 9 wherein both said mesh layers are formed of woven material.

11. An electrode strip for use in an electrochemical sensor for measuring a compound in a sample, comprising:

an elongated electrode support defining a sample transfer path for directional flow of the sample from an application point along said electrode support;

a working electrode in said sample transfer path said working electrode comprising an enzyme which catalyzes a reaction involving a substrate for said enzyme or a substrate catalytically reactive with an enzyme and a mediator which transfers electrons between said enzyme-catalyzed reaction and said working electrode to create a current representative of the activity of said enzyme and representative of the compound;

a reference or counter electrode in said sample transfer path; and a covering layer defining an enclosed space over the sample transfer path, the reference or counter electrode and said working electrode, said covering layer having an aperture for receiving sample into said enclosed space;

said aperture spaced away from and upstream of said electrodes in said sample transfer path and said reference or counter electrode spaced downstream of said working electrode in said sample transfer path.

12. The strip claimed in claim 11 in which said reference or counter electrode is spaced downstream of any portion of said working electrode in said sample transfer path.

13. The strip of claim 11 further comprising a plurality of superimposed mesh layers disposed along said sample transfer path between said electrodes and said covering layer.

14. The strip of claim 13 wherein said mesh layers have different mesh sizes.

15. The strip of claim 14 wherein said mesh layers comprise a first layer adjacent said electrodes and a second mesh layer interposed between said first layer and said covering layer, said second layer having a coarser mesh size than said first layer.

16. The strip of claim 15 wherein at least said second mesh layer is formed of woven material.

17. The strip of claim 16 wherein both said mesh layers are formed of woven material.

18. The strip of claim 15 wherein said mesh layers are surfactant coated, and said first layer contains a higher loading of surfactant than said second layer.

19. The strip of claim 18 wherein said mesh layers are of hydrophobic material and said surfactant coatings on said layers render them hydrophilic.

20. The strip of claim 15 wherein said sample transfer path is further defined by an area of hydrophobic insulating material disposed around and impregnating the periphery of the mesh layers.

21. The strip of claim 20 wherein both said mesh layers are formed of woven material.

* * * * *